US012765924B2

(12) United States Patent
Tsuang et al.

(10) Patent No.: US 12,765,924 B2
(45) Date of Patent: Oct. 20, 2026

(54) BONE SCREW FIXING ROD MANIPULATION SYSTEM

(71) Applicant: Chanpin Medtak Co., Ltd., New Taipei City (TW)

(72) Inventors: Fon-Yih Tsuang, Taipei City (TW); Chang-Chen Yang, Taipei City (TW); Yueh-Feng Chiang, Taipei City (TW); Po-Yi Liu, Taipei City (TW); Che-Yung Kuan, Taipei City (TW)

(73) Assignee: Chanpin Medtak Co., Ltd., New Taipei City (TW)

( * ) Notice: Subject to any disclaimer, the term of this patent is extended or adjusted under 35 U.S.C. 154(b) by 59 days.

(21) Appl. No.: 18/924,346

(22) Filed: Oct. 23, 2024

(65) Prior Publication Data

US 2026/0108282 A1 Apr. 23, 2026

(30) Foreign Application Priority Data

Oct. 22, 2024 (TW) ................................ 113140090

(51) Int. Cl.
*A61B 17/70* (2006.01)

(52) U.S. Cl.
CPC ........ *A61B 17/7088* (2013.01); *A61B 17/701* (2013.01); *A61B 17/7082* (2013.01); *A61B 17/7086* (2013.01)

(58) Field of Classification Search
CPC ............ A61B 17/7088; A61B 17/7086; A61B 17/7083; A61B 17/701
See application file for complete search history.

(56) References Cited

U.S. PATENT DOCUMENTS

2010/0249856 A1* 9/2010 Iott .................... A61B 17/7085 606/301
2014/0046388 A1* 2/2014 Reichen ............. A61B 17/7083 606/86 A

* cited by examiner

*Primary Examiner* — Amy R Sipp
(74) *Attorney, Agent, or Firm* — Wang Law Firm, Inc.

(57) ABSTRACT

A bone screw fixing rod manipulation system is provided, which includes a fixing member, a moving member and a gripping part. The fixing member has a first front end and a first distal end opposite to each other, the first front end is provided with a rod-receiving recess for accommodating and fixing the bone screw fixing rod. The moving member has a second front end and a second distal end opposite to each other, the second front end is provided with a rod-guiding notch for limiting and moving the bone screw fixing rod, and the second distal end is provided with a first thread. The gripping part has a receiving cavity and a rotatable threaded member, the receiving cavity accommodating space is used for accommodating the first distal end of the fixing member and the second distal end of the moving member, and a side wall of the receiving cavity is provided with a second thread engaged with the first thread. Wherein the rotatable threaded member is connected with the second distal end.

3 Claims, 6 Drawing Sheets

BONE SCREW FIXING ROD MANIPULATION SYSTEM

BACKGROUND OF THE INVENTION

1. Field of the Invention

The present disclosure relates to a bone screw fixing rod manipulation system, and more particularly to a bone screw fixing rod manipulation system applied to the spine.

2. Description of the Related Art

Various symptoms appear as humans grow older, especially symptoms of spinal nerve compression may appear for workers who have to stand or sit long hours for their jobs. Minimally invasive surgery on the lumbar spine is a usual treatment for the spinal nerve compression. During the surgery, vertebrae of specific sections are fixed without displacement by planting and fixing multiple bone screws therebetween, such that the vertebrae of the sections no longer compress the nerves by forbidding the patient to move the vertebrae of the sections (e.g., cannot bend over).

When performing the minimally invasive surgery on the lumbar spine, a bone screw fixing rod is required to, after the required number of bone screws are fixed on the spine, connect a rod part of each bone screw in series, so as to fix each bone screw along an orientation of the spine.

However, since the existing bone screw rod manipulation system clutches the bone screw rod with a fixed angle therebetween, which requires incisions of certain sizes for the bone screw rod to be placed into the body during the minimally invasive surgery. Therefore, it is difficult to reduce an area of the incisions, and risk of inflammation or infection and wound healing time of such incisions may be increased.

Therefore, to address the above-mentioned issues, an improvement of the bone screw fixing rod manipulation system needs to be made to reduce and minimize the size of the incision made during the minimally invasive surgery, so as to meet the requirement of minimizing the soft tissue damage at the surgical site.

SUMMARY OF THE INVENTION

In response to the above-referenced technical inadequacies, the present disclosure provides a bone screw fixing rod manipulation system capable of reducing a size of an incision made during the minimally invasive surgery.

In one aspect, the present disclosure provides a bone screw fixing rod manipulation system, which includes a fixing member, a moving member and a gripping part.

The fixing member has a first front end and a first distal end opposite to each other, the first front end is provided with a rod-receiving recess for accommodating and fixing the bone screw fixing rod.

The moving member has a second front end and a second distal end opposite to each other, the second front end is provided with a rod-guiding notch for limiting and moving the bone screw fixing rod, and the second distal end is provided with a first thread.

The gripping part has a receiving cavity and a rotatable threaded member, the rotatable threaded member is disposed at a top end of the gripping part and the receiving cavity is defined within the rotatable threaded member. The receiving cavity is used for accommodating the first distal end of the fixing member and the second distal end of the moving member, and a side wall of the receiving cavity is provided with a second thread engaged with the first thread. The rotatable threaded member is connected with the second distal end.

Preferably, a length of the first thread is greater than a length of the second thread.

Preferably, the cross-section shape of the bone screw fixing rod is not limited to a specific shape and may be circular, oval, square or polygonal.

Preferably, the bone screw fixing rod has two grooves generally parallel to each other two ends inside the rod-receiving recess of the fixing member are provided with first convex points, respectively, and the first convex points at the two ends inside the rod-receiving recess are parallel to each other and can be respectively engaged into the two grooves to fix the bone screw fixing rod.

Preferably, a second convex point is provided on a side wall of the rod-guiding notch of the moving member, and can be engaged into one of the two grooves groove to move the bone screw fixing rod.

Preferably, the fixing member and the moving member are attached to each other, when the rotatable threaded member is rotated to rotate the first thread along the second thread, the moving member can be controlled to move along the fixing member, so as to adjust an angle between the bone screw fixing rod and the fixing member, which is beneficial to place the bone screw fixing rod at a smaller angle into the incision made during the minimally invasive surgery to connect and fix multiple bone screws in series.

In summary, by rotating the rotatable threaded member to rotate the first thread provided at the second distal end of the moving member along the second thread provided at the side wall of the receiving cavity, an angle between the bone screw fixing rod and the fixing member can be adjusted according to an angle and a location of a to-be-fixed bone screw, such that the bone screw fixing rod and the fixing member can be placed into the incision made during the minimally invasive surgery at the most appropriate angle. Compared with the existing bone screw rod manipulation system, the size of the incision made during the minimally invasive surgery can be greatly reduced and minimized, so as to meet the requirement of minimizing the soft tissue damage at the surgical site.

BRIEF DESCRIPTION OF THE DRAWINGS

The objective, technical contents, advantages and effects of the present disclosure will be further appreciated and understood with reference to the detailed description of preferred embodiments and accompanying drawings.

DETAILED DESCRIPTION OF THE PREFERRED EMBODIMENTS

The present disclosure will be illustrated in detail below with preferred embodiments and accompanying drawings. It should be noted that, the shape and scale of the diagrams disclosed in each embodiment below are intended to account for the technical features of the present disclosure, and are not intended to limit the aspects of the present disclosure on the practical implementation.

The technical contents, objective and effects of the present disclosure will be disclosed completely and clearly hereinafter with reference to the accompanying drawings.

Figure 1:
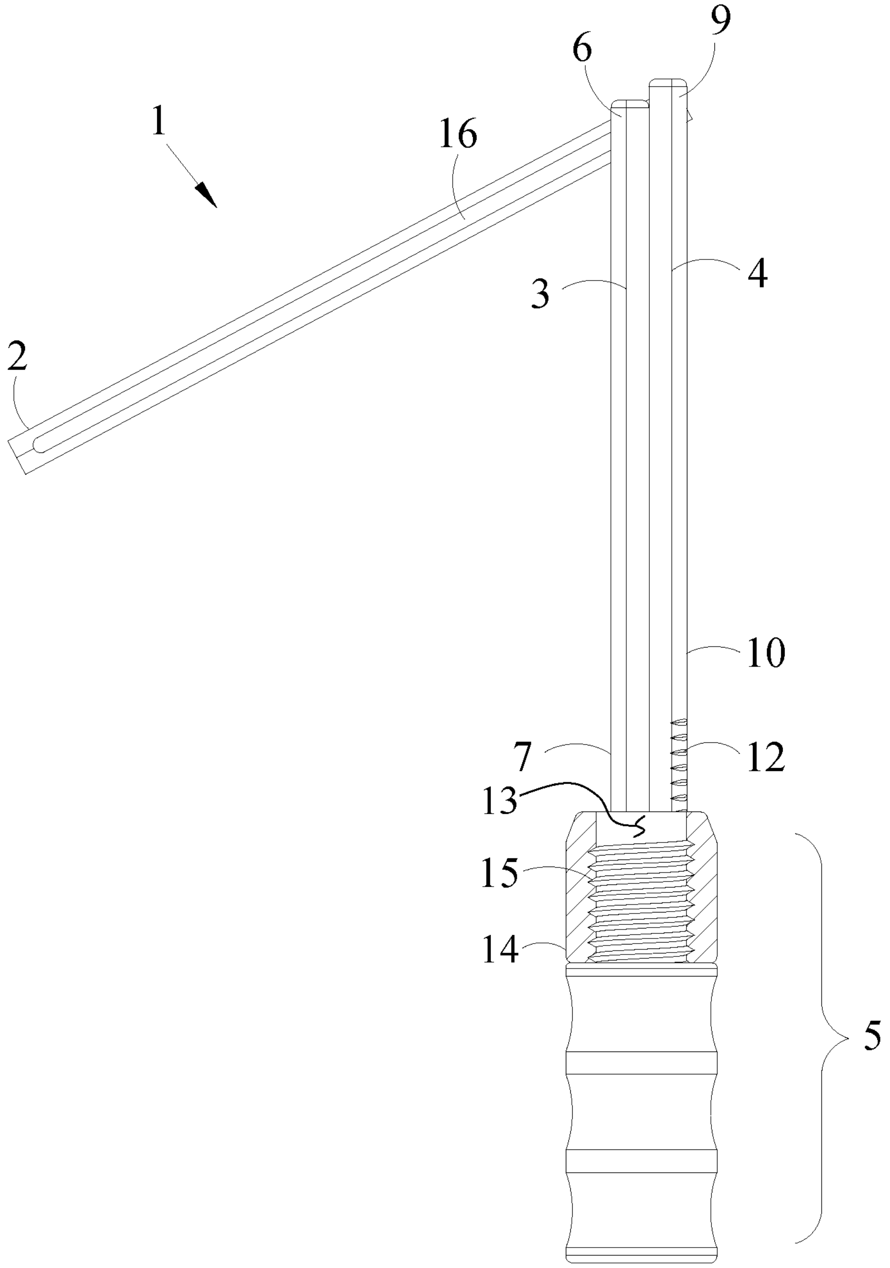
FIG. 1 is a side cross-sectional view of a bone screw fixing rod manipulation system in accordance with an embodiment of the present disclosure.
Figure 2:
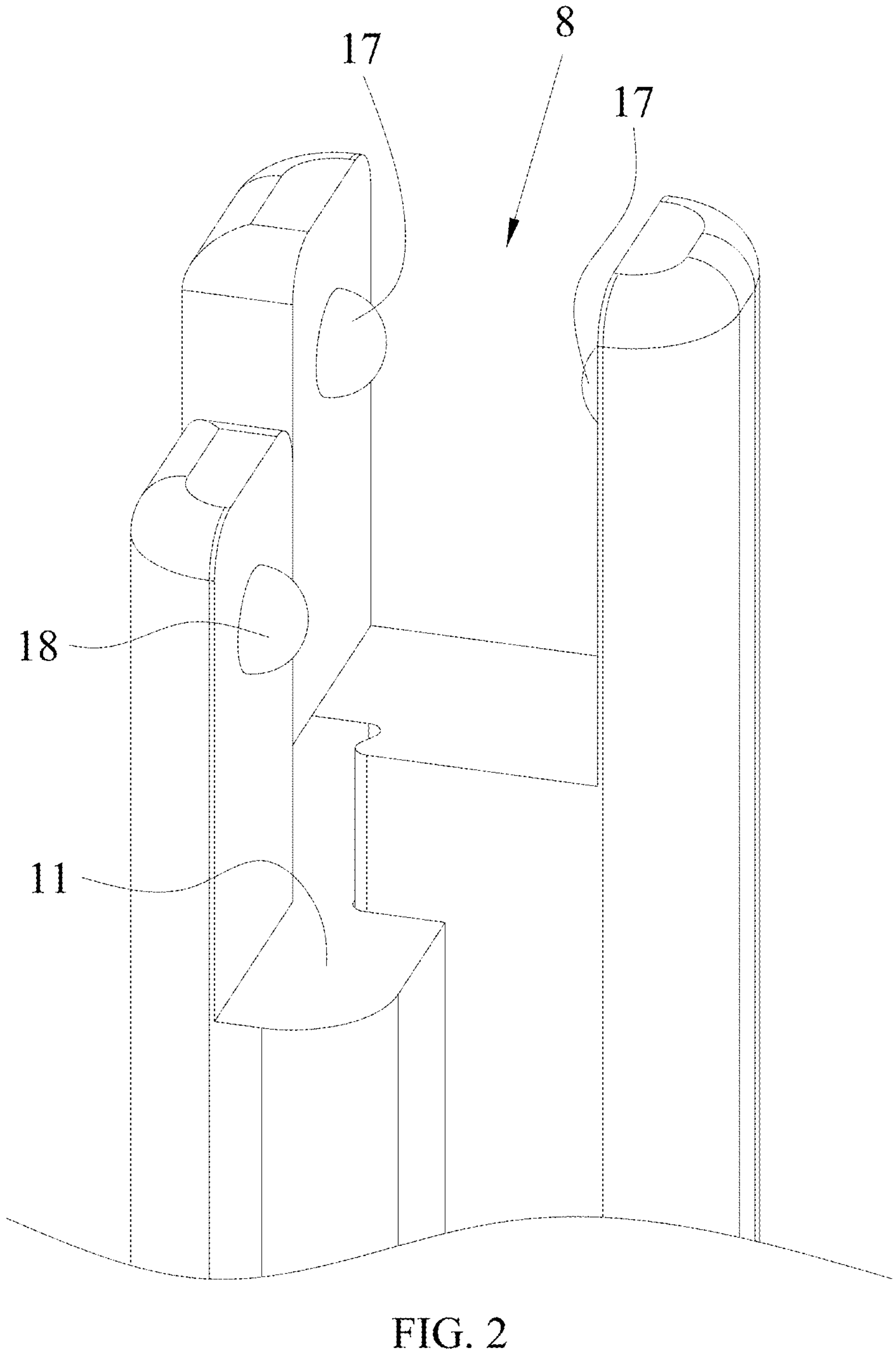
FIG. 2 is a partially enlarged perspective view of a first front end of a fixing member and a second front end of a moving member of the bone screw fixing rod manipulation system in accordance with an embodiment of the present disclosure.
Figure 3:
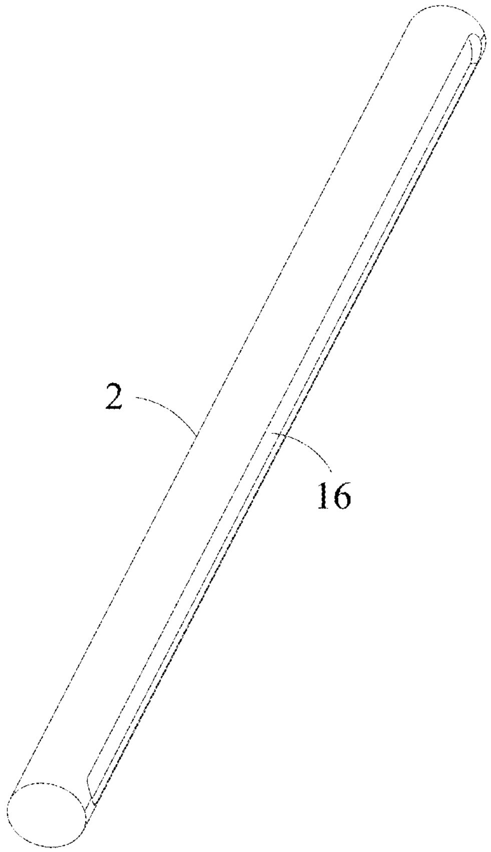
FIG. 3 is a three-dimensional view of a bone screw fixing rod of the bone screw fixing rod manipulation system in accordance with an embodiment of the present disclosure.
Figure 4:
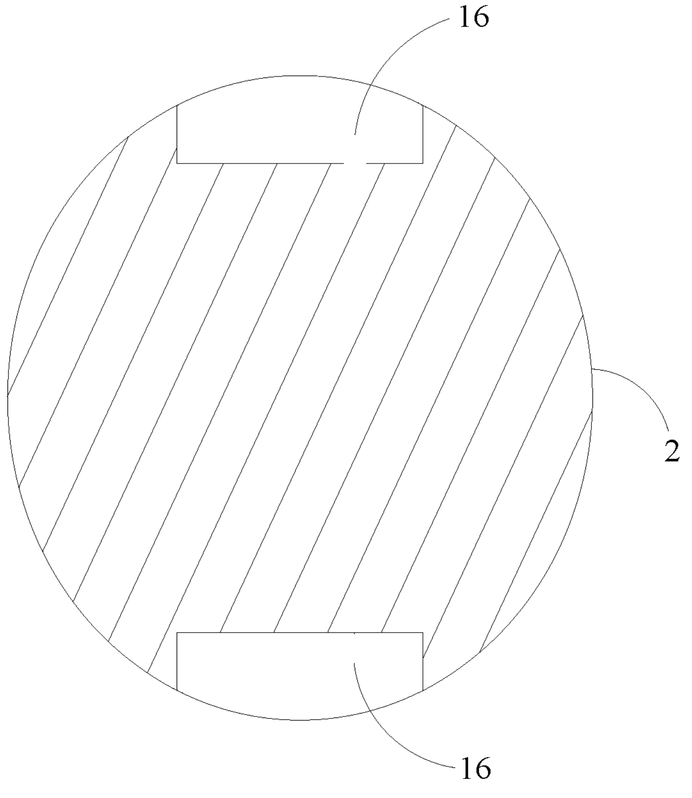
FIG. 4 is a cross-sectional view of the bone screw fixing rod of the bone screw fixing rod manipulation system in accordance with an embodiment of the present disclosure.

Reference is made to FIGS. 1 to 4, FIG. 1 is a side cross-sectional view of a bone screw fixing rod manipulation system in accordance with an embodiment of the present disclosure, FIG. 2 is a partially enlarged perspective view of a first front end of a fixing member and a second front end of a moving member of the bone screw fixing rod manipulation system in accordance with an embodiment of the present disclosure, FIG. 3 is a three-dimensional view of a bone screw fixing rod of the bone screw fixing rod manipulation system in accordance with an embodiment of the present disclosure, and FIG. 4 is a cross-sectional view of the bone screw fixing rod of the bone screw fixing rod manipulation system in accordance with an embodiment of the present disclosure.

It can be seen from FIGS. 1 to 4 that a bone screw fixing rod manipulation system 1 for a bone screw fixing rod 2 includes a fixing member 3, a moving member 4 and a gripping part 5.

The cross-section shape of the bone screw fixing rod 2 is not limited to a specific shape and may be circular, oval, square or polygonal.

The fixing member 3 has a first front end 6 and a first distal end 7 opposite to each other, the first front end 6 is provided with a rod-receiving recess 8 for accommodating and fixing the bone screw fixing rod 2.

The moving member 4 has a second front end 9 and a second distal end 10 opposite to each other, the second front end 9 is provided with a rod-guiding notch 11 for limiting and moving the bone screw fixing rod 2, and the second distal end 10 is provided with a first thread 12.

The gripping part 5 has a receiving cavity 13 and a rotatable threaded member 14, the rotatable threaded member 14 is disposed at a top end of the gripping part 5 and the receiving cavity 13 is defined within the rotatable threaded member 14. The receiving cavity 13 is used for accommodating the first distal end 7 of the fixing member 3 and the second distal end 10 of the moving member 4, and a side wall of the rotatable threaded member 14 defining the receiving cavity 13 is provided with a second thread 15 engaged with the first thread 12. The rotatable threaded member 14 is connected with the second distal end 10.

Preferably, a length of the first thread 12 is greater than a length of the second thread 15.

The bone screw fixing rod 2 is generally circular and has two grooves 16 generally parallel to each other. Two ends inside the rod-receiving recess 8 of the fixing member 3 are provided with first convex points 17, respectively, and the first convex points 17 at the two ends inside the rod-receiving recess 8 are parallel to each other and can be respectively engaged into the two grooves 16 of bone screw fixing rod 2 to fix the bone screw fixing rod 2.

A second convex point 18 is provided on a side wall of the rod-guiding notch 11 of the moving member 4, and can be engaged into one of the two grooves 16 to move the bone screw fixing rod 2.

Figure 5:
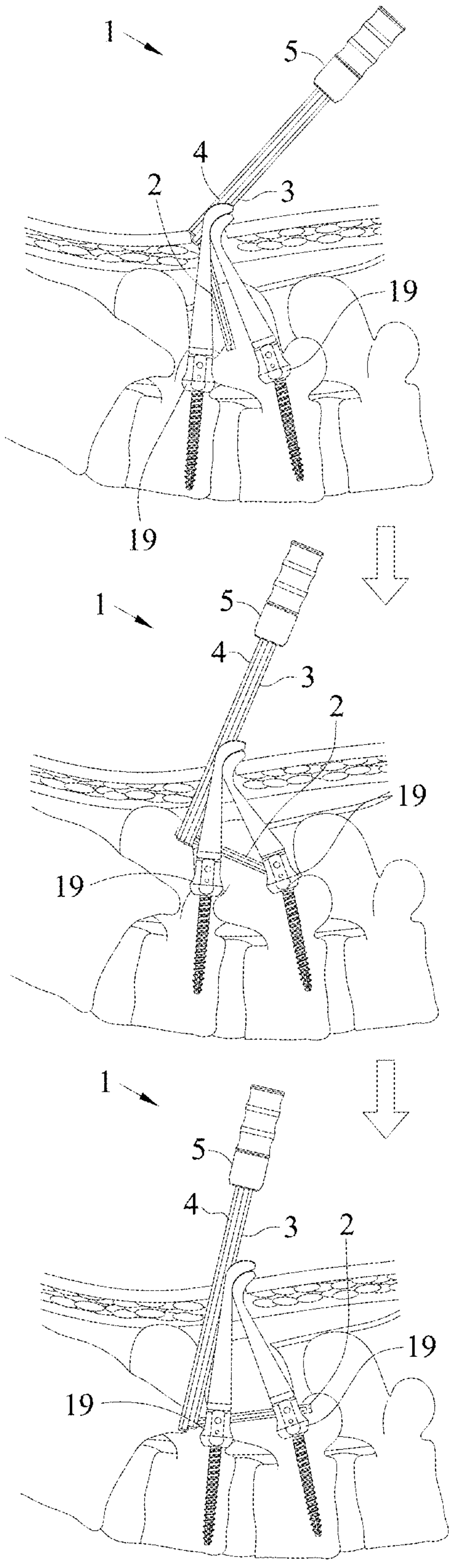
FIG. 5 is a schematic diagram showing a movement of the moving member made along the fixing member of the bone screw fixing rod manipulation system in accordance with an embodiment of the present disclosure.
Figure 6:
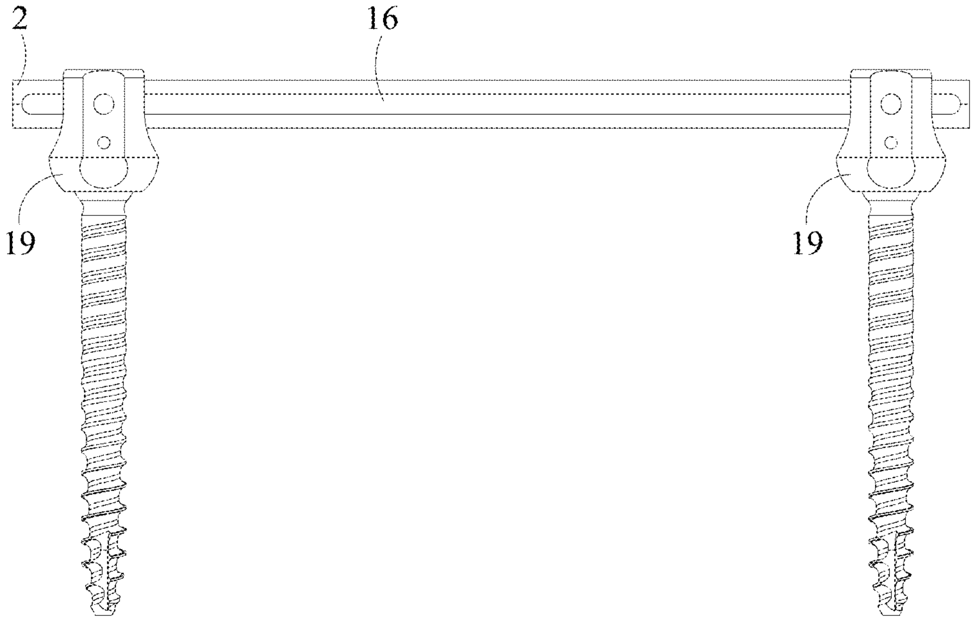
FIG. 6 is a schematic diagram showing bone screws being connected in series and fixed by the bone screw fixing rod in accordance with an embodiment of the present disclosure.

Reference is further made to FIGS. 5 and 6, FIG. 5 is a schematic diagram showing a movement of the moving member made along the fixing member of the bone screw fixing rod manipulation system in accordance with an embodiment of the present disclosure, and FIG. 6 is a schematic diagram showing bone screws being connected in series and fixed by the bone screw fixing rod in accordance with an embodiment of the present disclosure.

It can be seen from FIGS. 5 and 6 that the fixing member 3 and the moving member 4 of the bone screw fixing rod manipulation system 1 are attached to each other, when the rotatable threaded member 14 is rotated to rotate the first thread 12 along the second thread 15, the moving member 4 can be controlled to move along the fixing member 3, so as to adjust an angle between the bone screw fixing rod 2 and the fixing member 3, which is beneficial to place the bone screw fixing rod 2 at a smaller angle into the incision made during the minimally invasive surgery to connect multiple bone screws 19 in series and fix the bone screws 19.

In summary, by rotating the rotatable threaded member, the moving member can be moved along the fixing member, the angle between the bone screw fixing rod and the fixing member can be adjusted. Based on the angle of the location of the to-be-fixed bone screw, the bone screw fixing rod and the fixing member can be placed into the incision made during the minimally invasive surgery at the most appropriate angle. Compared with the existing bone screw rod manipulation system, the size of the incision made during the minimally invasive surgery can be greatly reduced and minimized, so as to meet the requirement of minimizing the soft tissue damage at the surgical site.

The present disclosure has been described above with preferred embodiments, but the description of preferred embodiments is not intended to limit the scope of the present disclosure. Many modifications and variations will be apparent to those having ordinary skill in the art without departing from the spirit and scope of the present disclosure. Therefore, the scope of the present disclosure should be defined by the appended claims.

What is claimed is:

1. A rod manipulation system for manipulating a bone screw fixing rod, the bone screw fixing rod having two grooves generally parallel to each other, the rod manipulation system comprising:

- a fixing member having a first front end and a first distal end opposite to each other, wherein the first front end is provided with a rod-receiving recess for accommodating and fixing the bone screw fixing rod;
- a moving member having a second front end and a second distal end opposite to each other, wherein the second front end is provided with a rod-guiding notch for limiting and moving the bone screw fixing rod, and the second distal end is provided with a first thread; and
- a gripping part having a rotatable threaded member being disposed at a top end of the gripping part and a receiving cavity defined within the rotatable threaded member, wherein the receiving cavity is used for accommodating the first distal end of the fixing member and the second distal end of the moving member, and a side wall of the rotatable threaded member defining the receiving cavity is provided with a second thread configured to be engaged with the first thread, wherein the rotatable threaded member is connected with the second distal end, wherein the fixing member and the moving member are attached to each other, wherein two ends inside the rod-receiving recess of the fixing member are provided with first convex points, respectively, and the first convex points at the two ends inside the rod-receiving recess are parallel to each other and configured to respectively engage into the two grooves of the bone screw fixing rod to fix the bone screw fixing rod, wherein a second convex point is provided on a side wall of the rod-guiding notch of the moving member, and is configured to engage with one of the two grooves of the bone screw fixing rod to guide movement of the bone screw fixing rod.

2. The rod manipulation system according to claim 1, wherein the second thread of the rotatable threaded member is configured to drive the first thread of the moving member and control the moving member to move along the fixing member, so as to adjust an angle between the bone screw fixing rod and the fixing member.

3. The rod manipulation system according to claim 2, wherein a length of the first thread is greater than a length of the second thread.

* * * * *